(12) United States Patent
Amaral et al.

(10) Patent No.: US 11,464,882 B2
(45) Date of Patent: Oct. 11, 2022

(54) DRY DIFFUSER APPARATUS AND METHOD

(71) Applicant: 1st Sense Technologies LLC, Charlotte, NC (US)

(72) Inventors: David Amaral, Charlotte, NC (US); Robert Blaylock, Tega Cay, SC (US)

(73) Assignee: 1st Sense Technologies LLC, Charlotte, NC (US)

( * ) Notice: Subject to any disclaimer, the term of this patent is extended or adjusted under 35 U.S.C. 154(b) by 230 days.

(21) Appl. No.: 16/739,871

(22) Filed: Jan. 10, 2020

(65) Prior Publication Data
US 2021/0213151 A1 Jul. 15, 2021

(51) Int. Cl.
*A61L 9/03* (2006.01)
*A01M 1/20* (2006.01)

(52) U.S. Cl.
CPC ........... *A61L 9/032* (2013.01); *A01M 1/2072* (2013.01); *A01M 1/2077* (2013.01); *A61L 2209/11* (2013.01); *A61L 2209/133* (2013.01); *A61L 2209/14* (2013.01); *A61L 2209/15* (2013.01)

(58) Field of Classification Search
None
See application file for complete search history.

(56) References Cited

U.S. PATENT DOCUMENTS

| | | | | |
|---|---|---|---|---|
| 5,175,791 | A * | 12/1992 | Muderlak | A61L 9/03 219/492 |
| 6,511,531 | B1 * | 1/2003 | Cartellone | A61L 9/16 96/222 |
| 7,648,127 | B2 | 1/2010 | Cittadina | |
| 7,651,077 | B1 | 1/2010 | Rosener et al. | |
| 9,364,575 | B2 | 6/2016 | Habbel | |
| 2005/0218243 | A1 | 10/2005 | Zobele et al. | |
| 2007/0034082 | A1 * | 2/2007 | Adair | B01D 53/32 96/63 |
| 2011/0110827 | A1 | 5/2011 | Yamamoto et al. | |
| 2013/0049236 | A1 | 2/2013 | Garon et al. | |
| 2013/0320574 | A1 | 12/2013 | Sickinger et al. | |
| 2014/0332990 | A1 | 11/2014 | Brosmith | |
| 2015/0075445 | A1 * | 3/2015 | Shi | A01M 13/00 119/712 |
| 2018/0154036 | A1 | 6/2018 | Davis et al. | |
| 2018/0369442 | A1 | 12/2018 | Kelsen | |
| 2019/0117820 | A1 | 4/2019 | Dam | |

FOREIGN PATENT DOCUMENTS

WO WO2017173516 10/2017

OTHER PUBLICATIONS

Benson, T. Aera Smart Home Fragrance Review. YouTube.com [online video] [retrieved on Nov. 17, 2021]. https://www.youtube.com/watch?v=NJIBa-CCWA0 (Year: 2017).*
International Search Report and Written Opinion for PCT Application PCT/US2021/012453, dated Mar. 18, 2021.

* cited by examiner

*Primary Examiner* — Jelitza M Perez
(74) *Attorney, Agent, or Firm* — Pearl Cohen Zedek Latzer Baratz LLP

(57) ABSTRACT

A dry diffuser is disclosed which avoids safety and transport issues typical of liquid diffusers, candles and wax melts and provides systematic controlled diffusion of fragrance (or other active material) over relatively long periods with a programmable user interface.

20 Claims, 5 Drawing Sheets

DRY DIFFUSER APPARATUS AND METHOD

BACKGROUND OF THE INVENTION

The most common fragrance diffusers are candles, wax melts, reed diffusers and liquid atomization devices. These devices utilize flame, high heat or liquids, which pose a risk of personal injury or damage to the property. Liquid fragrance diffusers in particular have the potential for spilling which may contaminate surfaces near the diffuser. The present invention is directed to dry diffuser technology which is safer and easier to transport. Additionally, the diffuser device allows for controlled diffusion of fragrance (or other active material) over relatively long periods. Methods of using the diffuser include use of programmable "smart" features for remote control of the diffuser operation and output.

SUMMARY OF THE INVENTION

In one aspect, the invention is a dry diffuser apparatus, comprising: a housing having an air intake aperture, an outlet aperture, and an air flow path within the housing from the air intake aperture to the outlet aperture; a non-liquid evaporative medium and an air filter provided in an integrated package received in the housing; an air foil in communication with the evaporative medium and proximate the outlet aperture; a fan positioned downstream of the air filter and upstream of the evaporative medium in the air flow path; a power supply; and programmable controls configured to control fan speed and fan duty cycle responsive to user input and responsive to properties of the evaporative medium and the air foil.

In another aspect, the invention is a method for providing timed diffusion of a substance from a dry evaporative medium, comprising: providing an apparatus having a housing having an air intake aperture, an outlet aperture, and an air flow path within the housing from the air intake aperture to the outlet aperture; providing a non-liquid evaporative medium and an air filter in an integrated package in the housing; providing an air foil in communication with the evaporative medium and proximate the outlet aperture; providing a fan in communication with a power supply, the fan being downstream of the air filter and upstream of the evaporative medium in the air flow path; and with the fan, directing air along the air flow path from the air intake aperture through the air foil to the outlet aperture in accordance with programmable controls setting the speed and duty cycle of the fan.

In embodiments, the apparatus is configured to communicate via an app, and the method includes communicating information about the apparatus, to a user and/or to a centralized database, with the app.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION

Figure 2:
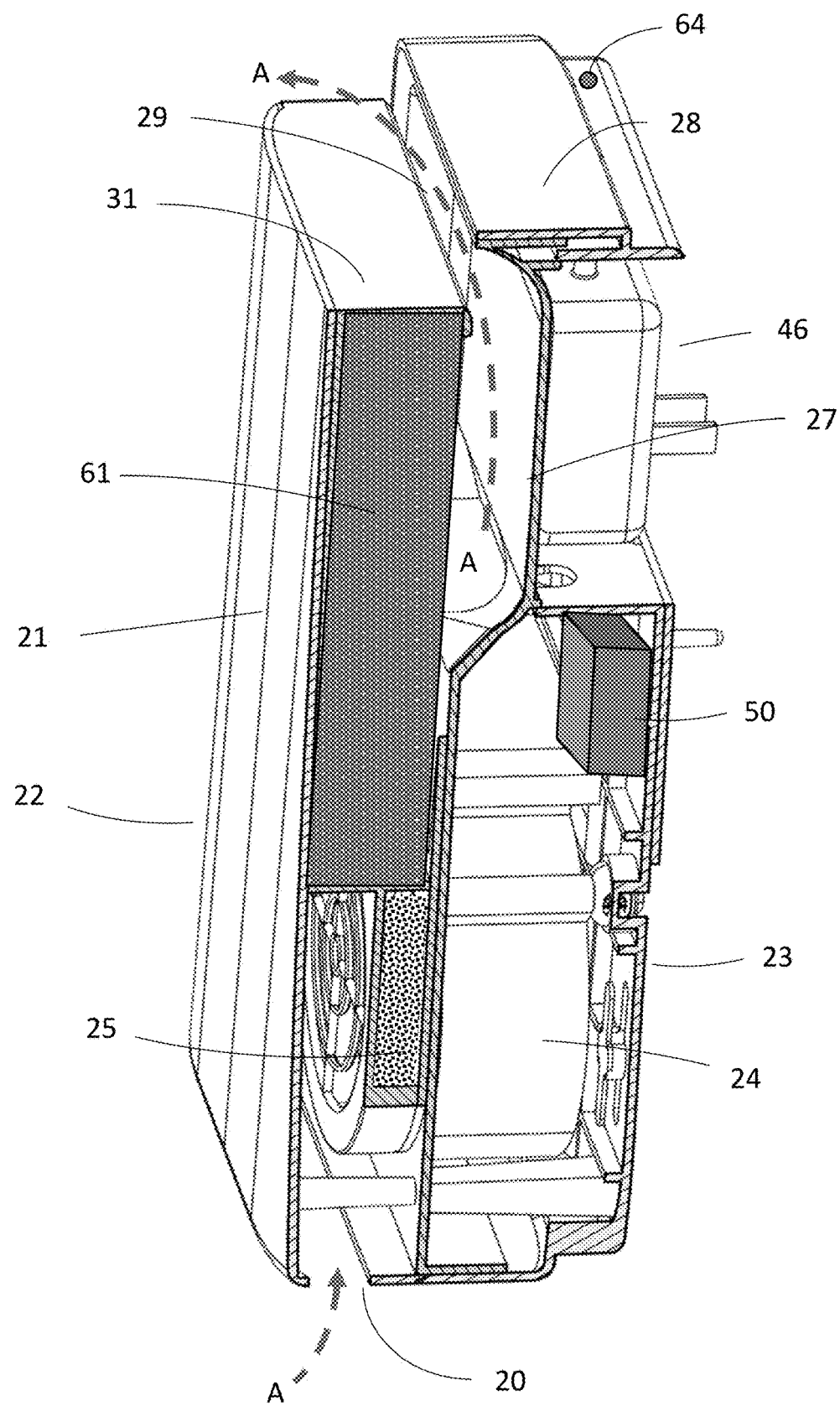
FIG. 2 is a section cutaway view of an apparatus according to an embodiment of the invention.

In the embodiment shown in FIG. 2, housing 22 comprises front portion 21 and rear portion 23 which in embodiments are adapted to be closed together such as with screws, clips, magnetic mounts or a hinge. A gap between the front and rear portions forms an air intake aperture 20 into the housing. Air flow is generated by fan 24 along an air flow path "A", such that air flows from the upstream air intake aperture 20, through filter 25, and fan 24, located downstream of the air intake, into an air foil area 27 and ultimately through downstream outlet aperture 29 and out of the device to provide diffused fragrance (or other active) to the surrounding area.

In embodiments, the apparatus comprises an integrated package or cartridge 34 received in housing 22. In the embodiment shown in FIG. 3, cartridge 34 comprises compartment 28 adapted to receive non-liquid evaporative medium 61 and air filter compartment 31 adapted to receive an air filter 25, adapted for installation over fan 24 to filter air flowing into fan 24.

Figure 3:
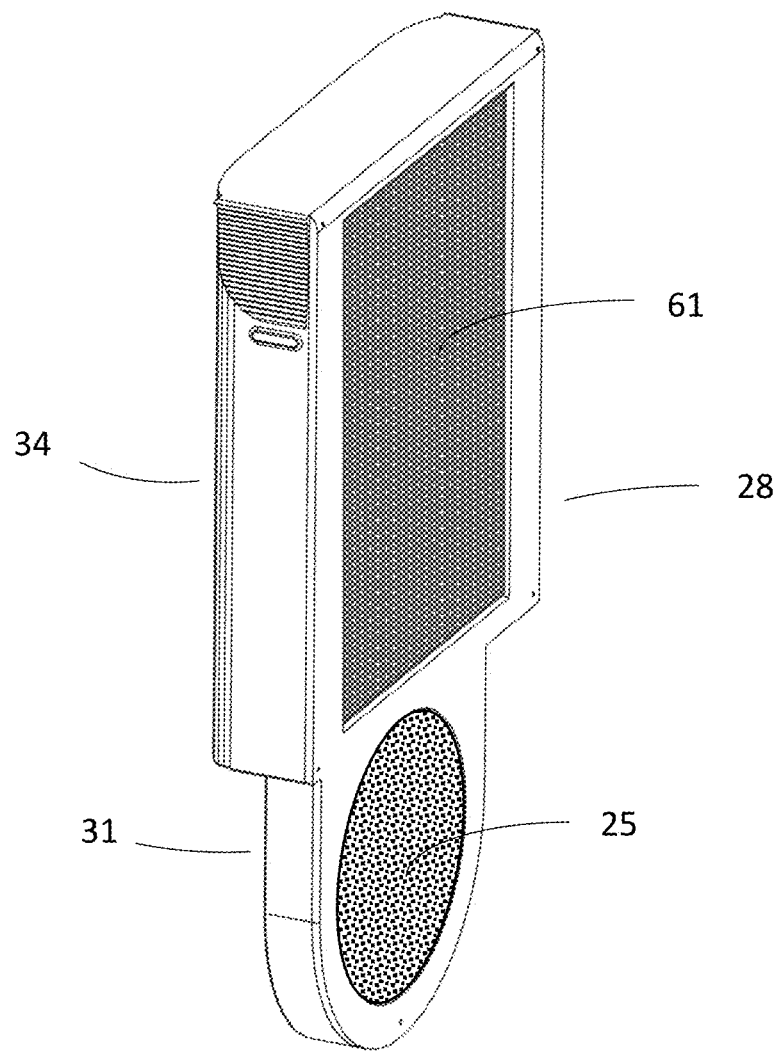
FIG. 3 is a detail view of a cartridge assembly that utilizes a housing according to an embodiment of the invention, including compartments for an air filter and a dry diffuser medium.

"Integrated", as used herein, means connected and used together. An embodiment of cartridge 34 shown in FIG. 3 shows the filter and evaporative medium integrated in one cartridge 34 which may be one piece, made of molded plastic, for example. However, a person having ordinary skill in the art may choose to integrate these elements in other ways, so that they are adapted to be attached and used together. Thus, an "integrated package" may be as simple as a clip holding the filter and evaporative media together so that they can be handled and installed together in a certain position with respect to one another. Having a single cartridge for the filter and the evaporative medium has an advantage in that the filter is replaced simultaneously with the evaporative medium, ensuring consistent filtering of air with minimal end user involvement. A peel off foil (not shown) may be provided to ensure stability of the evaporative medium as well as the air filter 25 prior to use. The filter is configured to be placed prior to or "upstream" of the fan 24 which prevents contamination of the evaporative medium 61 and fan 24. Placing filter 25 end-to-end in cartridge 34 with evaporative medium 61 also helps prevent contamination of the filter material.

Air filter 25 may be a porous material comprising carbon particles. Other air filter structures are known in the art and may be adapted to provide a filtered supply of air to the fan.

Any substance capable of being evaporated from dry media (broadly speaking, the "active") may be adapted for use with the invention, including fragrance, insect repellent, odor neutralizer or other diffusible substances. In embodiments, the active may be provided on a porous solid support, such as by infusing paper, porous plastic or other nonwoven fibrous material with a liquid active ingredient in an amount so that liquid does not settle or flow in the device. In other embodiments, the active may be volatile but solid at room temperature and may be in particulate form, for example. In the context of the invention, "dry" merely means that the active does not flow.

Fan 24 directs air through the fan and into the air foil 27 which is in communication with the evaporative medium 61 and proximate outlet aperture 29. Air foil may be designed to control residence time of airstream "A" in contact with the evaporative medium. Decreasing the volume of air space increases the velocity of the air over the medium which reduces the residence time of air in contact with the fragrance (or other active). In embodiments, air foil 27 includes low pressure zone and high pressure zone. In embodiments, outlet aperture 29 may be directionally adjustable.

Programmable controls (50) (shown schematically) are provided to control fan speed and fan duty cycle responsive to user input and responsive to properties of the evaporative medium and the air foil. The controls may be adapted for wireless communication with a remote device such as a smart phone using Bluetooth® technology or the like. Technology for remote control of the device is known to those of ordinary skill in the art and is not elaborated upon herein.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, on board or remote from the diffuser, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. As used herein, a "controller" and "controls" may refer to a computer onboard the diffuser, in a user's smart phone (or other device), or in a remote location, as will be clear from the context.

The programmable controls may be used to provide for automatic adjustment of fan speed and duty cycle in accordance with a predetermined profile of the dry evaporative medium over time. For example, and not by way of limitation, it may be desired to provide a uniform amount of diffused fragrance into a space. An evaporative medium containing the fragrance (or other active) on a support may tend to diffuse fewer molecules of fragrance per unit time into the surrounding area as the amount of active in the support falls. The programmable controls may compensate for the fall off in concentration by increasing the fan speed and/or duty cycle according to a predetermined schedule specific to the fragrance (or other active). Dry evaporative media may have a tendency to diffuse quickly at the outset and decay over time. The invention provides means for adjusting the mechanical features of the device (such as the fan) in accordance with known properties of the media. This relationship has not been leveraged in the prior art. Moreover, the profile of a particular medium may be recognized by the device, such as by providing RFID and or barcode identification which, when recognized by the device controls, triggers a predetermined duty cycle appropriate for the particular medium.

A low intensity heater (not shown) is optional. In embodiments a heater is not provided. However, in other embodiments, the diffuser further comprises a heater, and the programmable controls are further configured to control the heater temperature and duty cycle responsive to user input and/or properties of the evaporative medium and the air foil. For example, in the preceding example, where the concentration of active in the support declines over time and it is desired to maintain a constant output over time, the heater may be programmed to increase the temperature of the support over time to increase diffusion of the active. The protocols for heating and fan settings and duty cycles may be predetermined by testing the cartridge.

An electronic air purification component is optional. In embodiments an electronic air purifier is not provided. However, in other embodiments, the diffuser further comprises an air purifier such as an ionizer and/or UV light, and the programmable controls may be configured to control the air purification component.

Figure 1:
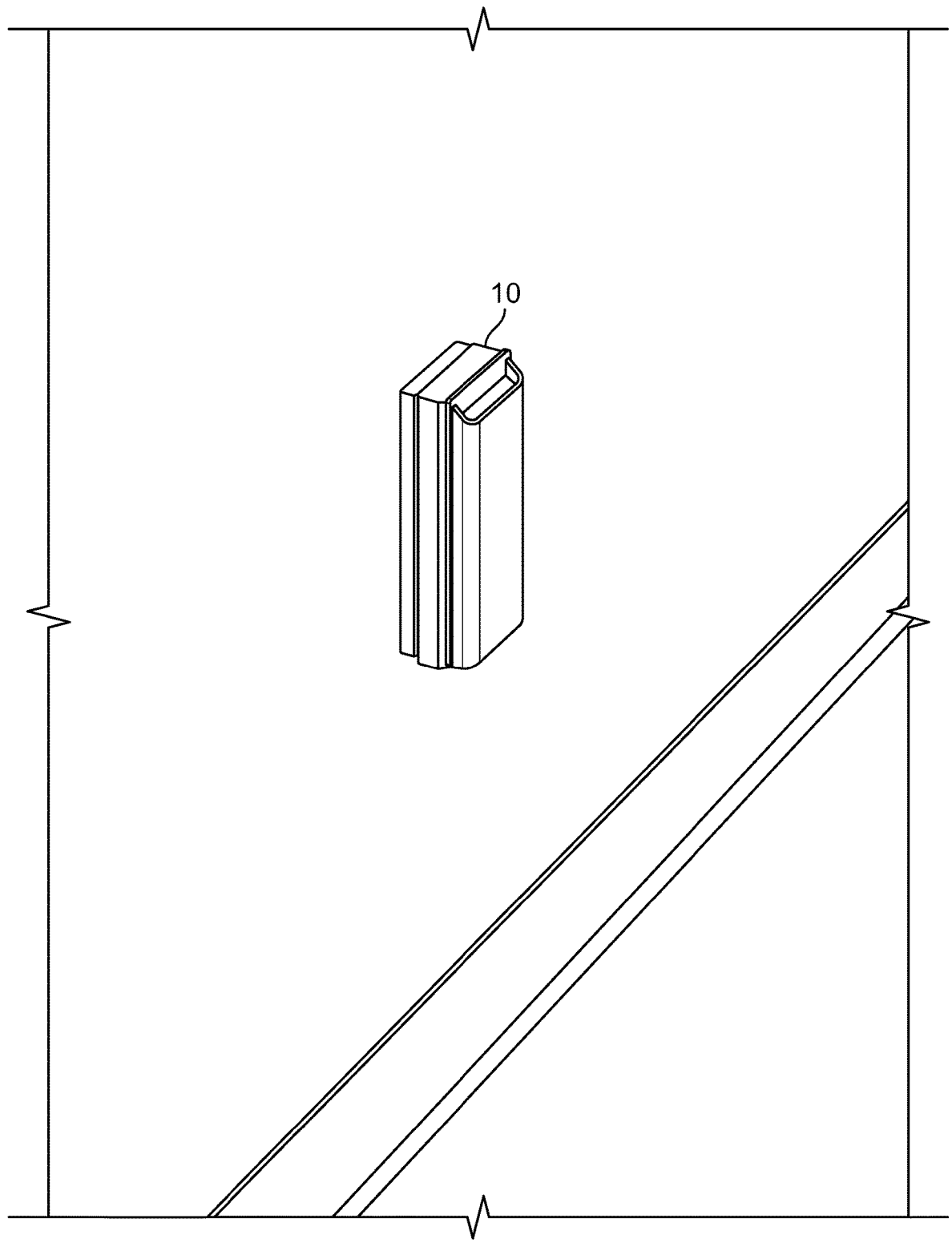
FIG. 1 is a perspective view of a diffuser apparatus according to an embodiment of the invention mounted on a standard electrical wall outlet.
Figure 4:
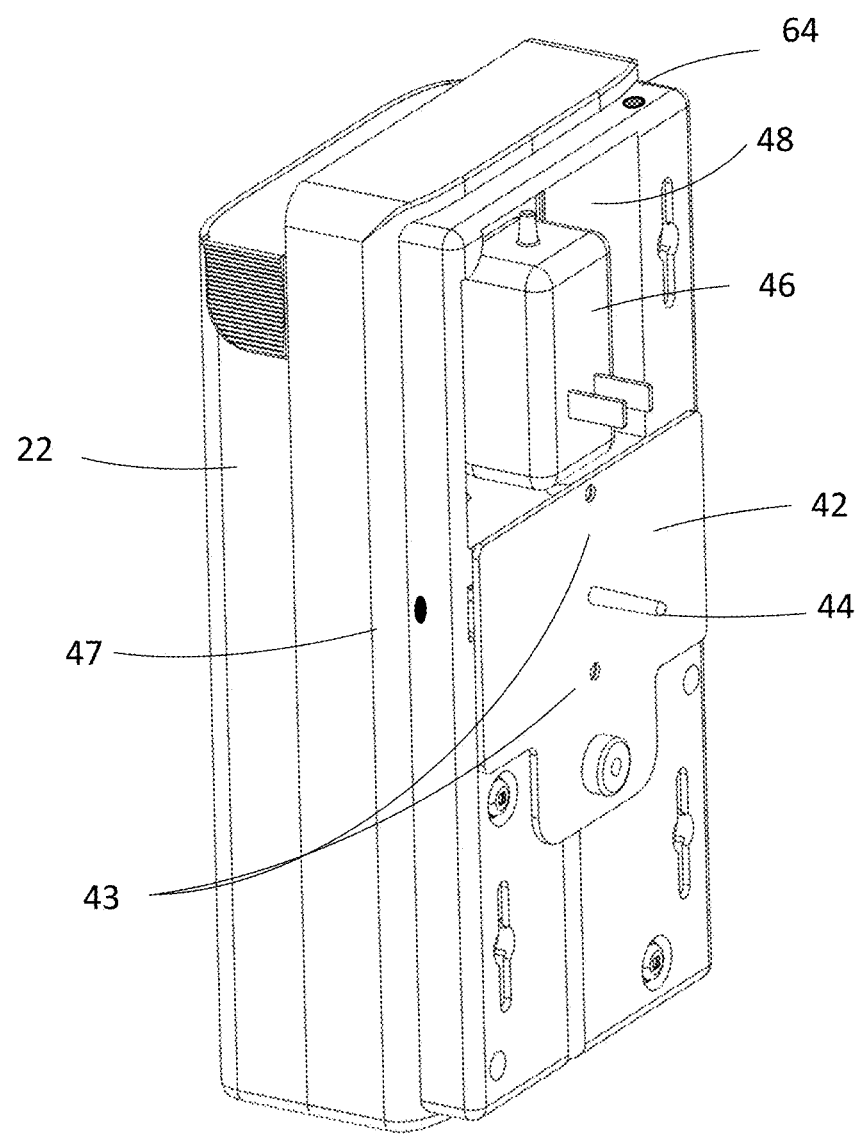
FIG. 4 is a rear view of a diffuser according to an embodiment of the invention, showing a mounting plate for mounting the diffuser on a standard electrical wall outlet.

FIG. 4 depicts an arrangement according to an embodiment of the invention, wherein power supply 46 may be concealed in recess 48 in housing 22 and the apparatus may be mounted over a standard electrical wall outlet, using mounting plate 42. In this embodiment, mounting plate 42 can be secured to a standard 110V U.S. wall outlet with a mounting screw positioned through one of the two mounting holes 43 and a non-conductive pin 44 extending from mounting plate 42 is positioned, sized and shaped to be received in a grounding plug of the outlet, stabilizing the mounting. Mounting plate locking tabs 45 (shown in FIG. 5) fit into slots within the rear portion 23 to secure housing 22. Release holes 47 on each side of the rear portion provides a means of releasing locking tabs 45 to remove housing 22 from wall plate 42. Alternatively, the device may be adapted for installation on a flat surface, such as a shelf. The power supply may be external to the housing. In still other embodiments the power supply is a battery. FIG. 1 shows the diffuser apparatus 10 installed on a wall outlet according to an embodiment of the invention.

Figure 5:
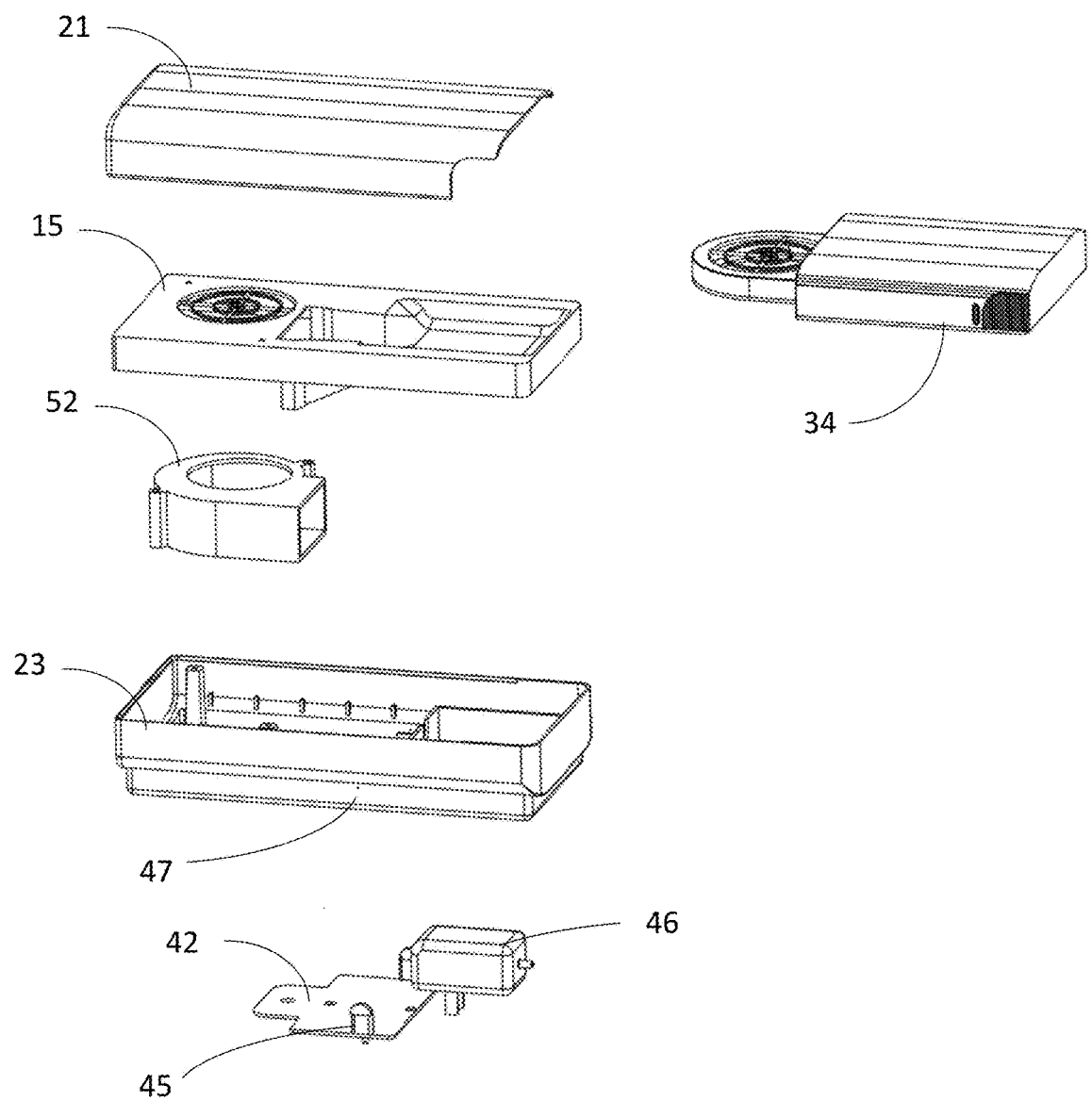
FIG. 5 is an exploded view of a diffuser according to an embodiment of the invention.

FIG. 5 depicts an apparatus according to an embodiment of the invention in exploded view, which demonstrates a simple assembly using cartridge 34, fan sub-housing 52, and air foil frame 15 in addition to front portion 21 and rear portion 23 of housing 22. In embodiments, front portion 21 and rear portion 23 may be hinged. Air foil 27 may be designed to create a high pressure zone and a low pressure zone at the surface of the evaporative medium 61 to control the rate at which fragrance (or other volatile substance) evaporates from the surface of the medium and the holding time within the device. In embodiments, air foil 27 is designed for a specific evaporative medium, according to the requirements of the evaporation and diffusion profile of the medium. In other embodiments, air foil 27 may be made adjustable to accommodate an evaporation and diffusion profile of different evaporative media.

In embodiments, the diffuser includes status light 69 or other user-visible display to communicate the status of the device. In embodiments, a dry diffuser apparatus according to the invention may be provided with wireless connectivity communicating with a user with an app, such as a smartphone app. The diffuser can be configured to detect a connected smartphone, to automatically turn on when the smartphone is in range and to turn off when the connected smartphone is out of range, for example. Alternatively, or in addition, data concerning the operation of the diffuser may be maintained on the app, so that a user is alerted when the cartridge requires changing, or if the location of the device has changed, or other device status information requires a user's attention. The app may be configured to send information about the apparatus, to a central database, including for example, cartridge change date/time, SKU of a cartridge installed, device settings, settings history, device run time, and location. The app may be configured for remote trouble shooting.

Modalities for providing connectivity between the diffuser and a smart phone (or other device) include Bluetooth® wireless communication protocol, Siri® personal assistant software Alexa® personal assistant software, and the like, as well as other modalities known in the art or developed for the same purpose. Communication between the diffuser and a remote location may be conducted through the smart phone, or other device, with an application such as Homegrid® or Nest® home network equipment. Information on the operation of the diffuser may be provided to a remote location where information is stored and processed. For example, monitoring the location of the diffuser may be used for security, triggering an alert if the diffuser is moved. A controller in a remote location may generate an alert when a cartridge or other component of the diffuser requires replacement. Usage data for a diffuser over time may (such as the type and amount of fragrance) may be compared with preselected information in a database, including customer-specific information, and used to manage the customer relationship. Collection of data from a diffuser wirelessly and processing the data in a remote location may have additional applications that will be apparent to the person of ordinary skill in the art.

In embodiments, duty cycle and intensity of the fan and/or heater (if any) over time may be set automatically based on reading computer readable information provided on a cartridge, a product SKU or RFID chip for example, and that information may be communicated to a user's smartphone or other computer, or to the remote location.

The description of the foregoing preferred embodiments is not to be considered as limiting the invention, which is defined according to the appended claims. The person of ordinary skill in the art, relying on the foregoing disclosure, may practice variants of the embodiments described without departing from the scope of the invention claimed. A feature or dependent claim limitation described in connection with one embodiment or independent claim may be adapted for use with another embodiment or independent claim, without departing from the scope of the invention.

What is claimed is:

1. A dry diffuser apparatus, comprising:
    a housing having an air intake aperture, an outlet aperture, and an air flow path within the housing from the air intake aperture to the outlet aperture;
    a non-liquid evaporative medium and an air filter in an integrated cartridge received in the housing;
    an air foil in communication with the evaporative medium and proximate the outlet aperture;
    a fan downstream of the air filter and upstream of the evaporative medium in the air flow path;
    a power supply; and
    programmable controls configured to control fan speed and fan duty cycle automatically in accordance with a predetermined profile of the evaporative medium over time and responsive to user input.

2. The dry diffuser apparatus according to claim 1, wherein the fan and/or the outlet aperture are directionally adjustable.

3. The dry diffuser apparatus according to claim 1, further comprising a heater, and wherein the programmable controls are further configured to control the heater temperature and duty cycle responsive to user input and properties of the evaporative medium and the air foil.

4. The dry diffuser apparatus according to claim 1, further comprising an air purifier, and wherein the programmable controls are further configured to control the air purifier duty cycle responsive to user input and properties of the air flow through the device.

5. The dry diffuser apparatus according to claim 1, wherein the power supply is removably received in the housing and is configured to be received in a standard electrical wall outlet.

6. The dry diffuser apparatus according to claim 4, further comprising a mounting plate for mounting the apparatus to a standard electrical wall outlet.

7. The dry diffuser apparatus according to claim 1, wherein the programmable controls include wireless connectivity with a user's smart phone and a centralized database.

8. The dry diffuser apparatus according to claim 1, wherein the evaporative medium includes fragrance, insect repellent, or odor neutralizer on a porous solid support.

9. The dry diffuser apparatus according to claim 1, wherein the integrated cartridge containing the air filter and the evaporative medium contains computer readable indicia and wherein the programmable controls are adapted to transmit information obtained from the computer readable indicia to a user's smart phone and/or a remote computer.

10. The dry diffuser apparatus according to claim 1, wherein the air foil has a high pressure zone and a low pressure zone in communication with the evaporative medium.

11. A method for providing timed diffusion of a substance from a dry evaporative medium, comprising:
    providing an apparatus having a housing having an air intake aperture, an outlet aperture, and an air flow path within the housing from the air intake aperture to the outlet aperture;
    providing the dry evaporative medium and an air filter in an integrated cartridge in the housing;
    providing an air foil in communication with the dry evaporative medium and proximate the outlet aperture;
    providing a low intensity heater in communication with a power supply, the heater being in proximate communication with the dry evaporative medium;
    providing an air purifier in communication with the power supply, the air purifier being downstream of the air filter and upstream of the dry evaporative medium in the air flow path;
    providing a fan in communication with the power supply, the fan being downstream of the air filter and upstream of the dry evaporative medium in the air flow path; and
    with the fan, directing air along the air flow path from the air intake aperture through the air foil to the outlet aperture in accordance with programmable controls setting the speed and duty cycle of the air purifier and fan, wherein
    the programmable controls provide for automatic adjustment of the fan speed and duty cycle in accordance with a predetermined profile of the dry evaporative medium over time.

12. The method according to claim 11, wherein the programmable controls provide for automatic adjustment of the fan speed and duty cycle in accordance with size and position of a high-pressure zone and a low pressure zone in the air foil proximate the dry evaporative medium.

13. The method according to claim 11, comprising altering the relative size and position of a high-pressure zone and a low pressure zone of the air foil in accordance with a predetermined profile of the dry evaporative medium over time.

14. The method according to claim 11, further comprising controlling the heater temperature and duty cycle responsive to user input and predetermined properties of the dry evaporative medium and the air foil.

15. The method according to claim 11, further comprising controlling the air purifier intensity and duty cycle responsive to user input and predetermined properties of the dry evaporative medium and the air foil.

16. A method for providing timed diffusion of a substance from a dry evaporative medium, comprising:

providing an apparatus having a housing having an air intake aperture, an outlet aperture, and an air flow path within the housing from the air intake aperture to the outlet aperture;

providing the dry evaporative medium and an air filter in an integrated cartridge in the housing;

providing an air foil in communication with the dry evaporative medium and proximate the outlet aperture;

providing a low intensity heater in communication with a power supply, the heater being in proximate communication with the dry evaporative medium;

providing an air purifier in communication with the power supply, the air purifier being downstream of the air filter and upstream of the dry evaporative medium in the air flow path;

providing a fan in communication with the power supply, the fan being downstream of the air filter and upstream of the dry evaporative medium in the air flow path; and with the fan, directing air along the air flow path from the air intake aperture through the air foil to the outlet aperture in accordance with programmable controls setting the speed and duty cycle of the air purifier and fan, wherein the power supply is concealed by a recess in the housing and is configured to be mounted on a standard electrical wall outlet, and wherein a rear portion of the housing comprises a mounting plate and a non-conductive post adapted to be received in a grounding plug of the wall outlet when the power supply is mounted on the wall outlet.

17. The method according to claim 11, comprising providing instructions to the programmable controls and communicating status information about the apparatus and the dry evaporative media with a user's smartphone.

18. The method according to claim 11, comprising providing instructions to the programmable controls and communicating status information about the apparatus and the dry evaporative media with a remote location wirelessly.

19. The method according to claim 11, comprising reading computer-readable information about the dry evaporative medium from indicia on the integrated cartridge and communicating the information with a user's smartphone and a remote location wirelessly.

20. The method according to claim 11, wherein a diffusive substance in the evaporative medium includes fragrance, insect repellent, or odor neutralizer.

* * * * *